March 25, 1969 R. YOSHIMURA Plant Pat. 2,872
AZALEA PLANT
Filed March 9, 1967
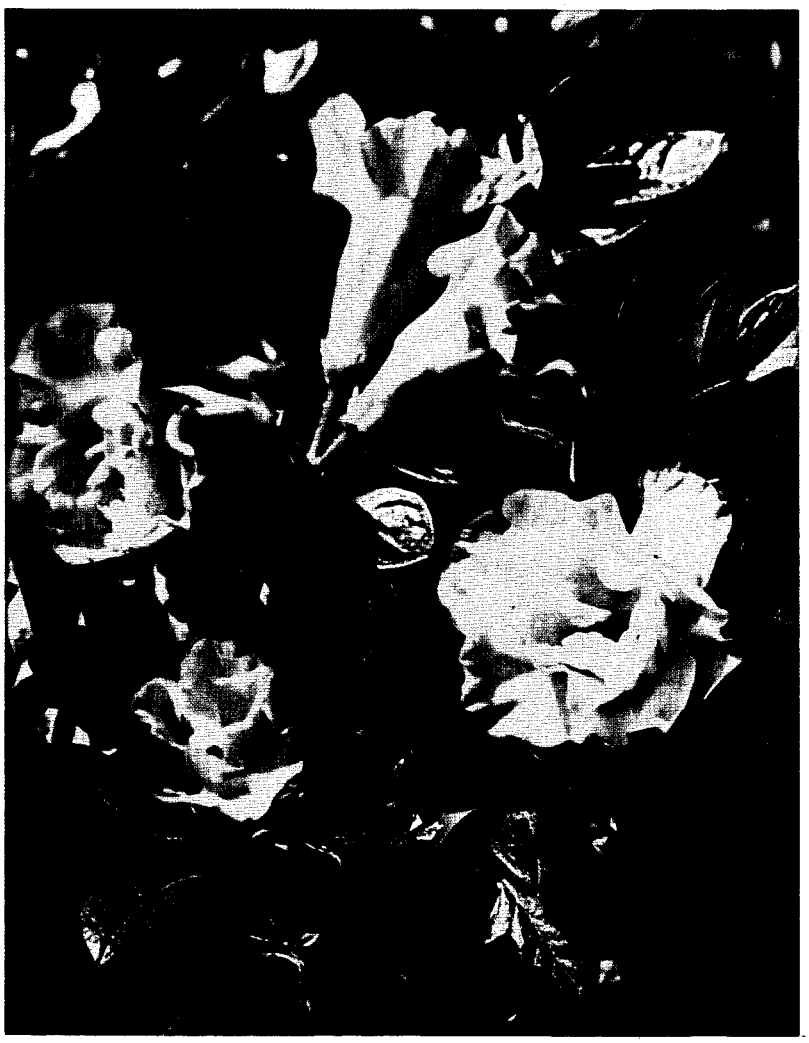
INVENTOR.
RAYMOND YOSHIMURA
BY J. F. Cuneo
ATTORNEY United States Patent Office Plant Pat. 2,872
Patented Mar. 25, 1969

2,872
AZALEA PLANT

Raymond Yoshimura, 827 S. Gladys,
San Gabriel, Calif. 91776

Filed Mar. 9, 1967, Ser. No. 622,004
Int. Cl. A01h 5/02
U.S. Cl. Plt.—57 1 Claim This invention relates to a new and distinct variety of azalea plant.

The plant resulted from cross-breeding a variety of azalea plant known in the trade as Mme. Memoria Sanders, a nonpatented variety, with another variety known as Chimes, which is also a nonpatented variety. The original plant was produced by me in 1956, at San Gabriel, Calif., using Mme. Memoria Sanders as the seed parent and Chimes as the pollen parent.

The flowers produced by the new variety of azalea are substantially campanulate in shape and are bright red in color. This variety bears flowers throughout the year but its peak blooming season occurs in the month of February in the coastal regions of southern California. The plant is a vigorous, upright, large variety.

Compared to its seed parent Mme. Memoria Sanders, the flowers of the new variety are Cardinal Red with parts of the flower shading to Indian Lake. The petals shade to white at the inner base portion whereas the flowers of the seed parent are much lighter in color being substantially a rose red. The flowers of the seed parent are more double and the plant itself is not as vigorous or as large as the plant of the new variety. The seed parent does not produce as much pollen as the new variety.

Compared to its pollen parent Chimes, the flowers of the new variety are a much brighter red than those of the pollen parent that are best identified as orange red in coloration and are definitely single. The flowers have a much longer life than those of the pollen parent, even though this plant is classed as more vigorous than the seed parent.

The new variety can be grown either as a predominantly upright bush or it can be grown as a tree. The plant has been reproduced asexually by cuttings and grafting performed by me at San Gabriel, Calif. The resulting plants and flowers produced by these asexual reproductions have all reproduced true, bearing all of the distinguishing characteristics of the new variety through the succeeding propagations of this variety; this variety cannot be reproduced true from seed.

The accompanying illustrations in full color show a typical specimen of the blooms, buds, and foliage. The colors are as true as it is possible to reproduce them by this type of color representation. A detailed description of the new variety of azalea plant follows and to facilitate identification of the important colors described in the specification, the designations adopted by the British Horticultural Colour Charts has been followed.

*The flower*

Locality where grown and observed: San Gabriel, Calif.
Flowers borne: A number of flowers are borne on a stem.
Continuity: The plant will bloom throughout the year but the peak blooming period occurs generally in February in the coastal region of southern California. The flowers will last on the plant from six to eight weeks in the winter months but usually last only three weeks on the plant during the summer months.
Bud:

*Before calyx breaks.*—Size—about three-eighths of an inch in diameter and from one-half to three-quarters of an inch in length.

*As calyx breaks.*—Color—predominantly green. sepals: shape—substantially elliptic; size—range from one-half to three-quarters of an inch in length.

*As first petal opens.*—Size—one and one-half to one and three-quarters of an inch in length, with the width being slightly less. Color—the color is predominantly Cardinal Red 822/1. Shape—the petals appear to be substantially round and are undulate. They arrange themselves compactly around the base and open up more toward the tip.

Bloom:

*Size.*—The blooms are from two and one half to three inches at the widest part.

*Petalage.*—Petals vary from five to nine in number.

*Form.*—Bloom is campanulate, opening quite wide at the outer end.

*Petals.*—Shape—the petals are substantially orbicular at the outer end and become slightly pointed or more obtuse at the base. The margin is undulate. Some of the petals have one or more notches in the margin. Color—the predominant color is Cardinal Red 822/1, however, some parts of the flower shade to Indian Lake 826/1. When one approaches the inner base portion the petal becomes almost white.

*General color effect.*—The general overall color effect is the Cardinal Red 822/1.

*Flower longevity.*—The flowers last up to eight weeks during the cooler winter months and show a duration of about three weeks during the warmer summer months.

*Reproductive organs*

Stamens: Stamens vary from none to seven.
Filaments: Filaments are the same in number as the stamens. Color—the filaments are substantially the color of the flower.
Anthers: Anthers vary from none to seven in number. Color—the anthers are somewhat darker than the dark color of the flower.
Pollen: Quantity—average quantity. Color—whitish.
Ovaries: Ovaries are not visible being covered with fine white hairs.

*The plant*

Foliage:

*Leaves.*—Leaves are broadly elliptic with the tip apiculate and the base attenuate. Margin of the leaf is slightly ciliate. The surface of the leaves is slightly puberulent. Leaves are alternate.

*Petiole.*—Petiole is about five-eighths of an inch long.

*Veins.*—Veins are pinnate in their arrangement and are more prominent on the underside of the leaf than on the upper side; back of petiole and main veins strigose.

*Size of leaves.*—The leaves are from one to one and one-quarter inches in width and from two to two and one-quarter inches in length when full grown.

*Color of leaves.*—Upper side of leaf—Parsley Green oo962. Under side of leaf—Willow Green ooo862.

Growth habit: Plant is classed as a moderate grower. The plant can grow up to fifteen inches in one year during the early growth period and if permitted, the plant could reach a height of six feet. This variety can be grown either as a predominantly upright bush or it can be trained to form a tree.

Main stems: When trained as a bush the principal stems can be up to one inch in diameter. When trained as a tree the trunk will reach a diameter of one and one-quarter inches or slightly more.

Having described my invention, I claim:

1. The new and distinct variety of azalea plant substantially as herein shown and described, characterized particularly as to novelty by the slightly double, campanulate, predominantly Cardinal Red blooms that have small areas shading to Indian Lake, borne in great profusion during the winter months with many blooms on a stem, by its flowering habit that extends substantially throughout the year, by the long life of the blooms particularly during the winter months, and by its vigorous, upright growth habit.

No references cited.

ROBERT E. BAGWILL, *Primary Examiner.*